United States Patent [19]

Okamoto et al.

[11] Patent Number: 5,761,335

[45] Date of Patent: Jun. 2, 1998

[54] APPARATUS FOR FLASH REMOVAL AND OPTICAL INSPECTION OF O RINGS

[75] Inventors: Katsuya Okamoto; Yasuyuki Nishimura; Hisayuki Oga, all of Arida, Japan

[73] Assignee: Mitsubishi Cable Industries, Ltd., Amagasaki, Japan

[21] Appl. No.: 607,767

[22] Filed: Feb. 27, 1996

[30] Foreign Application Priority Data

Mar. 1, 1995 [JP] Japan ................... 7-068633

[51] Int. Cl.$^6$ ............... G06K 9/00; B07B 1/28; B65G 47/248
[52] U.S. Cl. ............... 382/141; 198/402; 209/674
[58] Field of Search ............... 382/141, 149, 382/152, 153, 142, 143; 348/91, 92, 131; 356/376, 237; 366/108, 109; 264/9, 161; 425/806; 364/478.18, 478.1, 468.01, 468.17, 468.19, 475.09; 451/33; 209/540, 674; 198/402, 407

[56] References Cited

U.S. PATENT DOCUMENTS

| | | | |
|---|---|---|---|
| 3,732,917 | 5/1973 | Deubel | 165/120 |
| 4,258,507 | 3/1981 | Majors et al. | 451/327 |
| 4,759,074 | 7/1988 | Iadipaolo et al. | 382/152 |
| 4,808,001 | 2/1989 | Brenden et al. | 356/394 |
| 4,817,184 | 3/1989 | Thomason et al. | 382/141 |
| 5,325,443 | 6/1994 | Beatty et al. | 382/147 |
| 5,588,068 | 12/1996 | Longest et al. | 382/141 |

Primary Examiner—Leo H. Boudreau
Assistant Examiner—Brian P. Werner
Attorney, Agent, or Firm—Armstrong, Westerman, Hattori, McLeland, & Naughton

[57] ABSTRACT

An apparatus for inspecting an O ring which detects surface flaws of O rings by successively sending O rings by a conveyor, projecting light and inputting pictures of O rings, and processing the pictures. The apparatus is provided with a vibrating screening machine for separating products and flashes removed from the products and feeding the products of O rings to the conveyor.

13 Claims, 10 Drawing Sheets

APPARATUS FOR FLASH REMOVAL AND OPTICAL INSPECTION OF O RINGS

BACKGROUND AND SUMMARY OF THE INVENTION

This invention relates to an apparatus for inspecting an O ring which detects a surface flaw by projecting light on an O ring, inputting a picture of the O ring, and processing the picture.

In a conventional manufacturing process of O rings, flashes are formed on vulcanized O rings, and it is necessary to remove these flashes from the O rings as products. In order to remove the flashes, an apparatus for refrigerating and removing flash has been generally used. This apparatus for refrigerating and removing flash removes flashes from O rings by embrittling the O rings owing to cooling power of liquefied nitrogen or liquefied carbonic acid gas and bumping plastic medium (polycarbonate) on the O rings at a high speed. Consequently, a mixture of products and flashes removed from the products is left after removal, and the products and flashes are conventionally separated by hand or by using a separator. In a well-known method for inspecting existence of a flash, a crack, a surface flaw, and difference in size of an O ring, O rings are automatically inspected by successively feeding the O rings by a conveyor, projecting light and inputting pictures of the O rings through a CCD camera, and performing picture processing. However, in the conventional method for inspecting an O ring, only one side of each O ring is inspected.

It is bothersome to manually separate products and flashes removed from the products, and in case of using a separator, the apparatus as a whole becomes large-scaled which produces a tremendous noise and can be used only for one size of O rings. Moreover, it is sufficient to inspect only one side of each O ring for examination in flashes, cracks, and size differences, but it is necessary to inspect both sides of each O ring for examination in surface flaws in order to prevent oversights and ensure reliability. Only one side of each O ring has been conventionally inspected because a speed for inspection is extremely high, 150 per minute for example, and it is difficult to accurately invert O rings on a conveyor at a high speed in correspondence with the inspection speed.

It is therefore an object of the present invention to provide an apparatus for inspecting an O ring which inspects surface flaws of only O rings as products after removal of flashes without manually separating the products and the flashes removed from the products.

It is another object of the present invention to provide an apparatus for automatically inspecting surface flaws of O rings with certainty.

BRIEF DESCRIPTION OF THE DRAWINGS

The present invention will be described with reference to the accompanying drawings, in which.

DESCRIPTION OF THE PREFERRED EMBODIMENTS

Preferred embodiments of the present invention will now be described with reference to the accompanying drawings.

Figure 1:
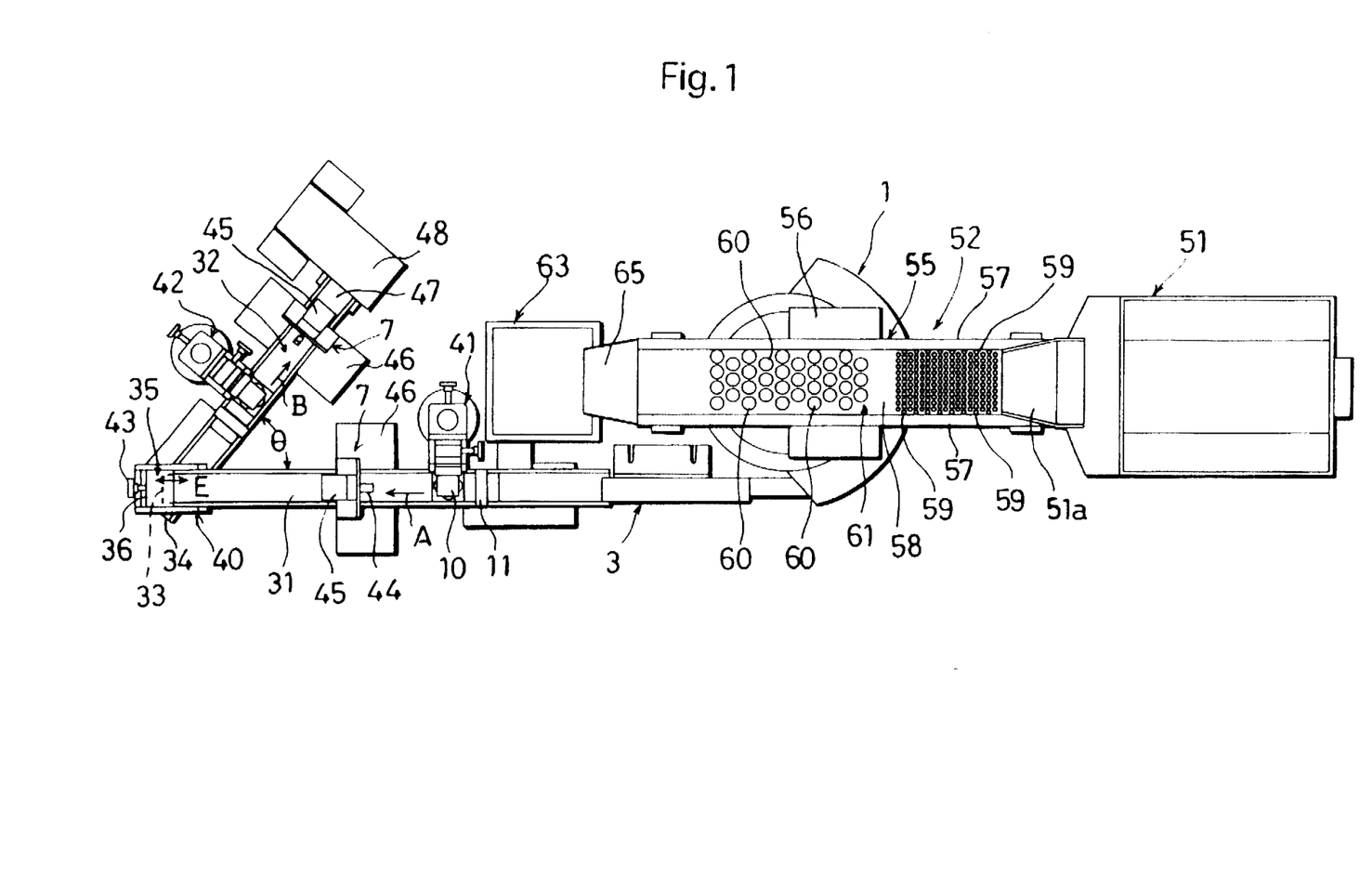
FIG. 1 is a top plan view of an apparatus for inspecting an O ring of the present invention.
Figure 2:
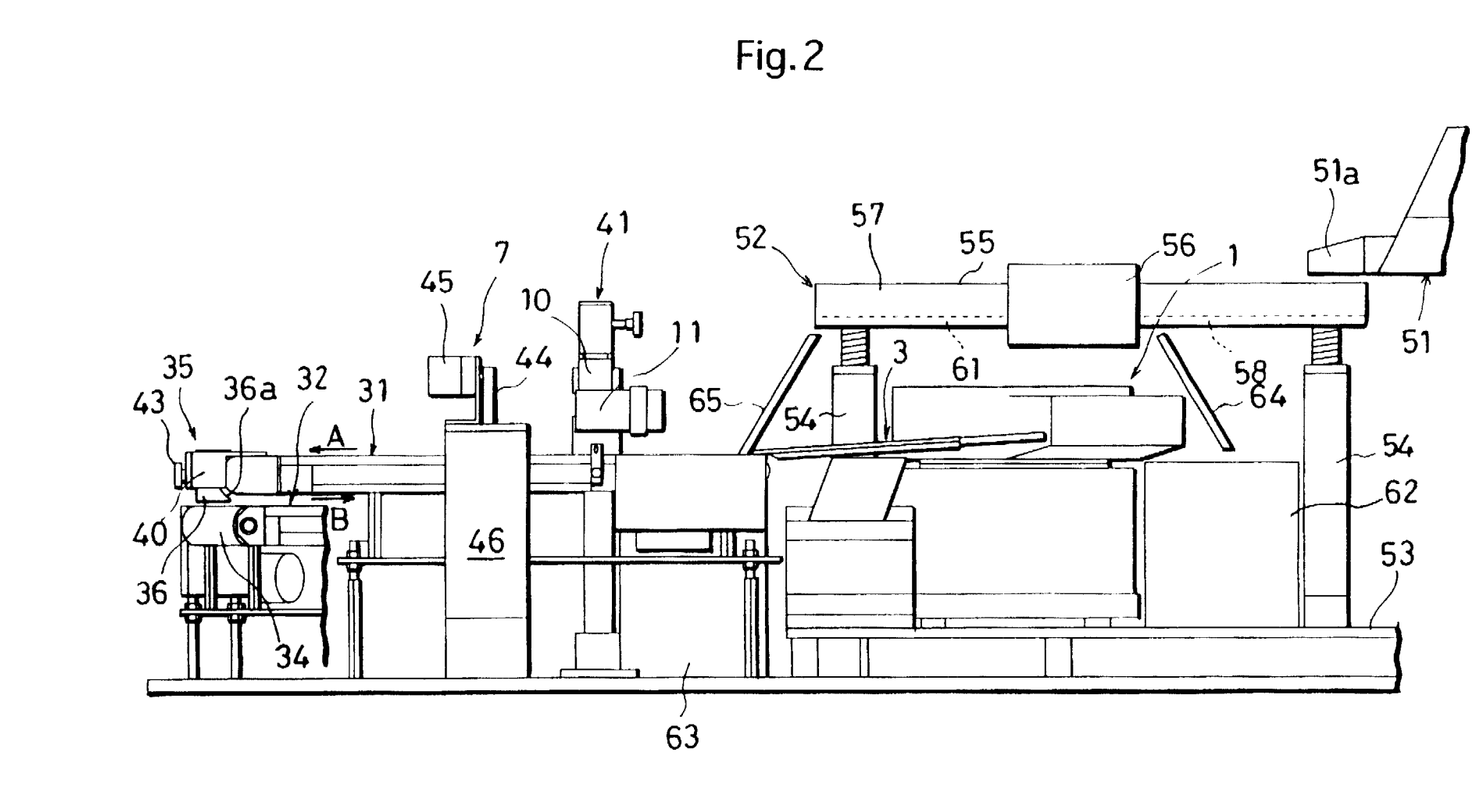
FIG. 2 is a front view of the apparatus for inspecting an O ring.
Figure 3:
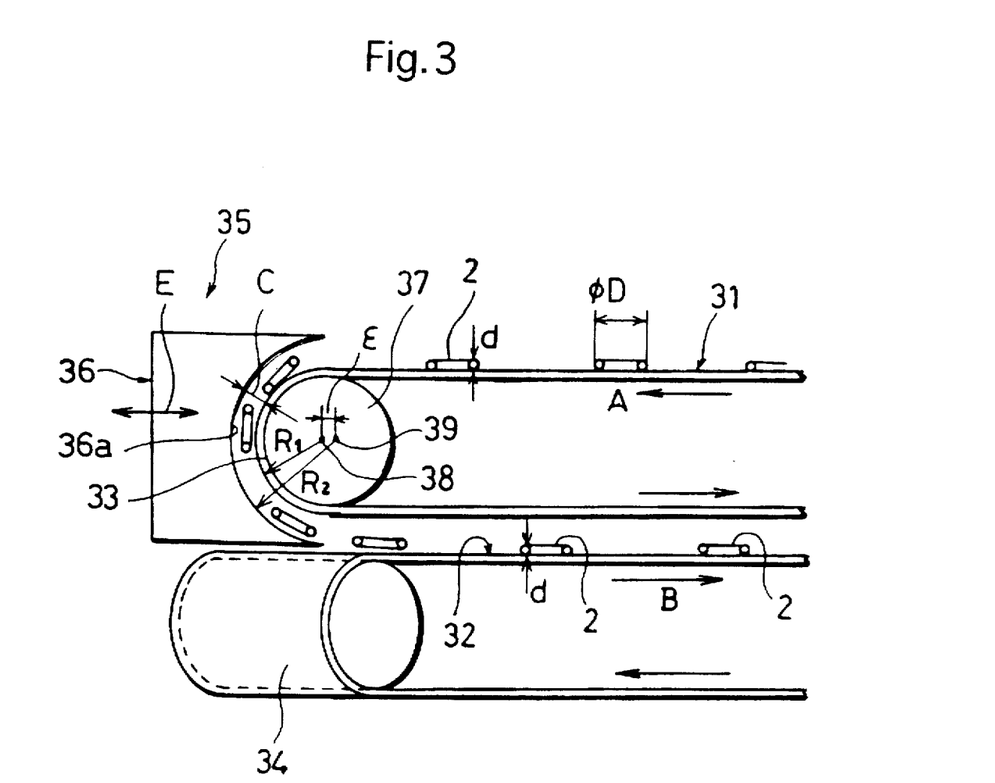
FIG. 3 is a front view in section of the apparatus for inspecting an O ring.
Figure 4:
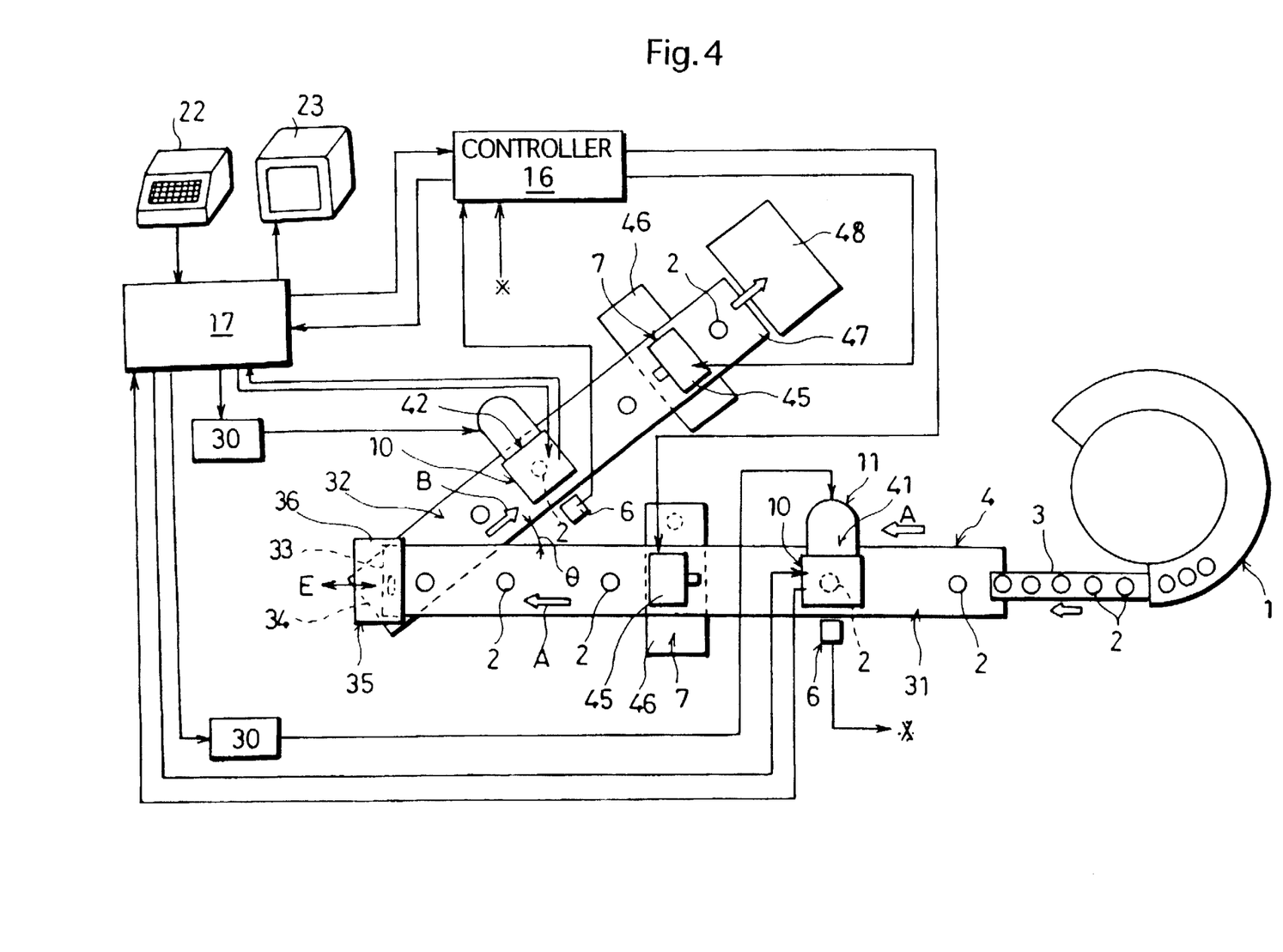
FIG. 4 is an explanatory view of a whole construction of the apparatus for inspecting an O ring.

In a top plan view of FIG. 1, a front view of FIG. 2, and explanatory views of a construction in section of FIG. 3 and FIG. 4, 31 is a first conveyor of an endless flat belt type and 32 is a second conveyor of an endless flat belt type, and both of them have surfaces of a bright color, for example, white, and send O rings 2 toward arrows A and B respectively. Each conveyor 31, 32 is continuously driven to run by a driving motor which is not shown in the attached drawings, therefore O rings 2 are sent continuously, and a U-turn portion 33 at an rear end side of the first conveyor 31 and a U-turn portion 34 at a front end side of the second conveyor 32 are arranged to have a vertical predetermined space between each other and lie one upon another when viewed in a plane of projection.

In a plane view as shown in FIG. 1 and FIG. 4, the first conveyor 31 and the second conveyor 32 cross at the U-turn portions 33, 34 at an acute angle θ of approximately 15° to 60°, and feeding direction of O rings 2 becomes opposite at the acute angle θ from the arrow A to the arrow B. 35 is an inverting means arranged at the rear end side of the first conveyor 31, i.e. at the U-turn portion 33 in the illustration. An O ring 2 fed toward the arrow A by the first conveyor 31 is turned over and transferred to the second conveyor 32 by the inverting means 35, and the second conveyor 32 receives the O ring 2 and feeds it toward the arrow B.

41 and 42 are a first inspecting means and a second inspecting means respectively, and each of them illuminates from a direction intersecting perpendicularly with the surface of the first conveyor 31 or the second conveyor 32, i.e. from upward toward a vertical direction in the illustration, processes a picture of a ring-shaped white portion 21 (see FIG. 8) formed by a reflection of a surface of an O ring 2, and detects a surface flaw. The inverting means 35 turns the O rings 2 over, therefore both sides of each O ring 2 are inspected through the first and second inspecting means 41, 42.

O rings 2 are fed from a hopper 51 (Flashes are removed from O rings 2 as products by a removing machine such as an apparatus for refrigerating and removing flash which is not shown in the attached drawings, and the products and flashes are fed to the hopper 51 beforehand.) to a screening machine 52, from the screening machine 52 to a parts feeder 1, and are successively sent from the parts feeder 1 to a front end (an upstream end) of the first conveyor 31 through a feeder for straight advance 3.

As shown in FIG. 1 and FIG. 2, the screening machine 52 comprises props 54 arranged on a base 53, a guide way 55 supported by the props 54, and an oscillating element 56 for vibrating the guide way 55. The guide way 55 comprises side walls 57 and a bottom wall 58 which becomes a vibration plate 61 having numerous small holes 59 of diameters smaller than inner diameters of O rings 2 as products and numerous big holes 60 of diameters larger than outer diameters of O rings 2, and the vibration plate 61 is freely attached to or separated from the side walls 57. A group of small holes formed by the numerous small holes 59 is arranged at an upstream portion of the vibration plate 61, and a group of big holes formed by the numerous big holes 60 is arranged at a midstream portion of the vibration plate 61.

O rings 2 as products and flashes removed from the O rings 2 are fed from a feeding portion 51a of the hopper 51 to an upstream end portion of the guide way 55. The products and flashes in the guide way 55 are screened by the vibration plate 61 oscillated by the oscillating element 56. O rings 2 do not drop from the small holes 59 and only small flashes drop because the diameters of the small holes 59 are smaller than the inner diameters of O rings 2, and O rings 2 as products drop from the big holes 60 because the diameters of the big holes. 60 are larger than the outer diameters of O rings, and big flashes which are larger than the big holes 60 and have passed the group of big holes drop from a downstream end of the guide way 55.

A small flash receiver 62 is arranged under the group of small holes, the parts feeder 1 is arranged under the group of big holes, and a big flash receiver 63 is arranged under the downstream side of the guide way 55. A flash guide plate 64 is arranged between the group of small holes and the small flash receiver 62 and is supported by a supporting member not shown in the attached drawings, and a flash guide plate 65 is arranged between the downstream end of the guide way 55 and the big flash receiver 63 and is supported by a supporting member not shown in the attached drawings. The small flashes which have dropped from the group of small holes are guided by the flash guide plate 64 and are contained in the small flash receiver 62, the products of O rings 2 which have dropped from the group of big holes are fed to the parts feeder 1, and the big flashes which have dropped from the downstream end of the guide way 55 are guided by the flash guide plate 65 and are contained in the big flash receiver 63.

In FIG. 1 to FIG. 4, the inverting means 35 is provided with an inversion guide 36 having a curved concave 36a for surrounding the U-turn portion 33 at the rear end side of the first conveyor 31 with a predetermined space C and guiding inversions of O rings 2. In the illustration shown in FIG. 3, the curved concave 36a of the inversion guide 36 is a circular arc of approximately 180° having a radius of $R_2$ and centering around a point 39 which is eccentric from a center of rotation 38 of a belt pulley 37 toward the upstream side for a little distance ε.

It is desirable to arrange so that the predetermined space C is adjustable corresponding to sizes of O rings. For example, it is possible to adjust the space C by screwing a knobbed bolt 43 which is rotatable and kept at a fixing frame for installation 40 into a tapped hole (not shown in the attached drawings) of the inversion guide 313, rotating the knobbed bolt 43 by hand, and moving the inversion guide 36 back and forth as shown with an arrow E.

In FIG. 3, the predetermined space C is decided by using a feeding speed, wire diameters d, and outer diameters D of O rings 2.

Next, an example of concrete structure and operation (an inspecting method) of the first inspecting means 41 and the second inspecting means 42 are going to be explained below. In FIG. 4 and FIGS. 1, 2, each of the first conveyor 31 and the second conveyor 32 are provided with a CCD camera 10 in the middle thereof, and a coaxial downward light projecting lamp 11 is attached to the CCD camera 10. It is preferable to arrange the camera 10 and the lamp 11 in a stage of XYZ axes in order to place (adjust) the camera 10 and the lamp 11 at appropriate positions corresponding to positions of O rings 2 successively sent by the conveyor 31 or 32. The position where the camera 10 and the lamp 11 are placed becomes a place for inspection, and a sensor 6 is arranged in order to detect O rings 2 sent to the place for inspection by the conveyor 31, 32.

As shown with a mark X in FIG. 4, a detection signal of the sensor 6 of the first conveyor 31 is inputted into a controller 16. A detection signal of the sensor 6 of the second conveyor 32 side is also inputted into the same controller 16. A device for discharging articles of poor quality 7 is placed on each downstream side from the places for inspection. Each device for discharging articles of poor quality 7 comprises, for example, a member 44 for throwing O rings toward a horizontal direction by horizontally and momentarily moving on a surface of the conveyor 31, 32, an actuator 45, and a box for receiving articles of poor quality 46. The actuator 45 operates on receipt of a signal from the controller 16 so that the member 44 throws O rings of poor quality from the conveyor 31, 32 into the box for articles of poor quality 46. A box for articles of good quality 48 for receiving O rings 2 of good quality is placed at a rear end (downstream end) 47 of the second conveyor 32.

Each CCD camera is provided with an electric shutter which shutter speed is extremely high, for example, 1/2000 sec. When an O ring detection signal is sent from the sensor 6 to the controller 16, an instruction signal from the controller 16 is sent to the CCD camera through a picture processing means 17, and the O ring 2 on the conveyor 31 or the conveyor 32 is illuminated by the lamp 11 and photographed by using the CCD camera 10.

Figure 5:
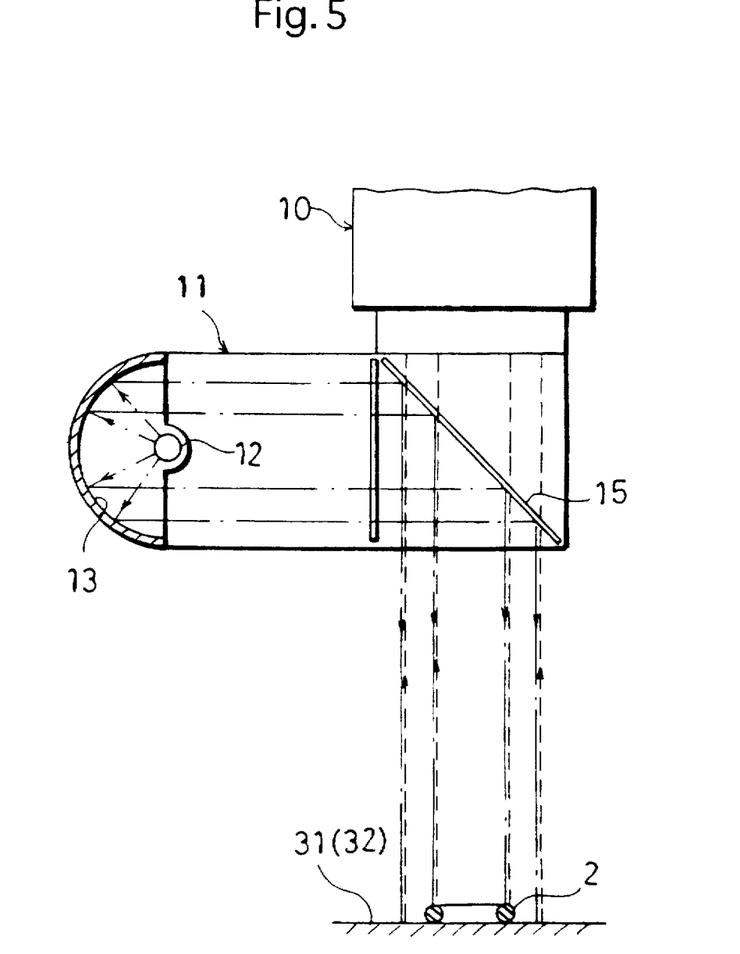
FIG. 5 is an explanatory view of a coaxial downward light projecting lamp and picking up a picture.

As illustrated in FIG. 5, the lamp 11 is arranged to have a horizontal optical axis which intersects perpendicularly with an optical axis of an end lens side of the CCD camera 10, and the lamp 11 comprises a light source 12 such as a halogen lamp, a concave mirror 13 for inverting light into a horizontal light beam, and a half mirror 15 arranged to have an inclination of 45°. The half mirror 15 have light reflectance of 50% and light transmissivity of 50%, and the optical axis of the lamp 11 is turned by 90° after reflection to coincide (be coaxial) with the vertical optical axis of the CCD camera 10. The light having the optical axis which is coaxial with the optical axis of the CCD camera 10 is designated as a coaxial downward light, and as shown in FIG. 5, a coaxial downward light is projected upon an O ring 2 on the conveyor 31 or the conveyor 32, light is reflected on a surface of the O ring 2 and a surface of the white conveyor 31 or the conveyor 32, and light transmitting through the half mirror 15 is incident upon the end lens side of the CCD camera 10.

Figure 7:
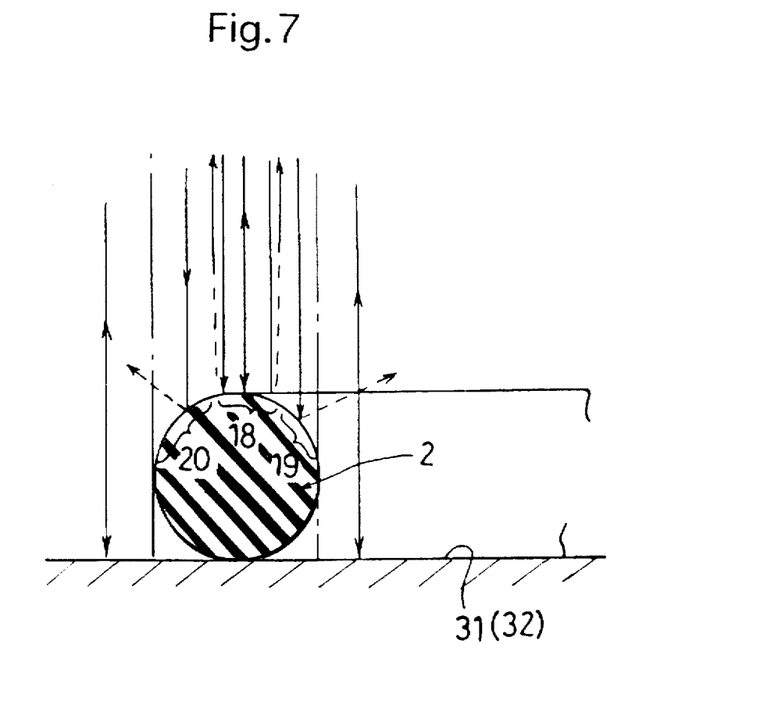
FIG. 7 is an explanatory view of a method for inspecting an O ring.

At this moment, as shown in FIG. 5 and FIG. 7, the coaxial downward light is reversed by 360° (a situation of approximate total reflection) at the vicinity of a top 18 of the surface of the O ring 2 and at the surface of the conveyor 31 or the conveyor 32 and is incident upon the end lens side of the CCD camera 10.

As shown in FIG. 4, an electrical connection is arranged so that a signal from each CCD camera 10 is sent into a picture processing means 17 such as a microcomputer, and the picture processing means 17 and a monitor 23 are electrically connected so that a picture as described below is indicated on the monitor 23. 22 is a controlling portion and is connected to the picture processing means 17.

Figure 8:
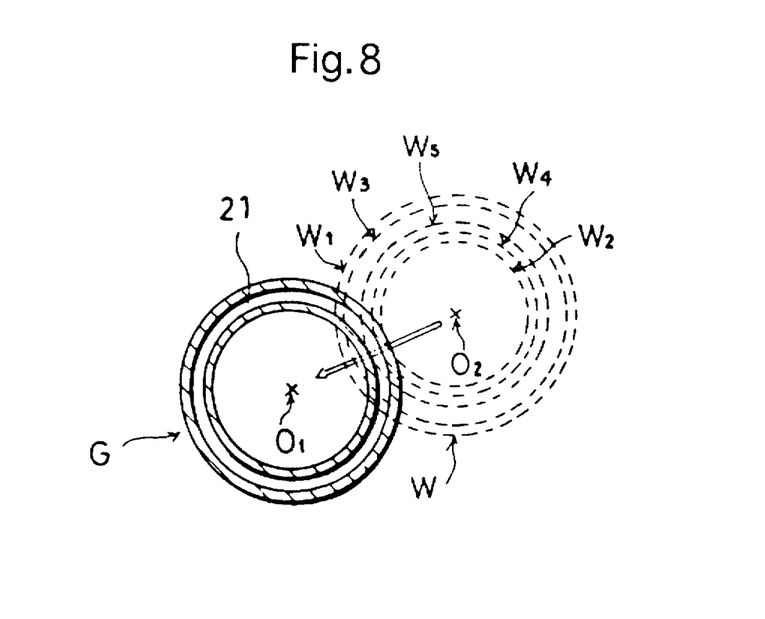
FIG. 8 is an explanatory view of a method for picture processing.
Figure 9:
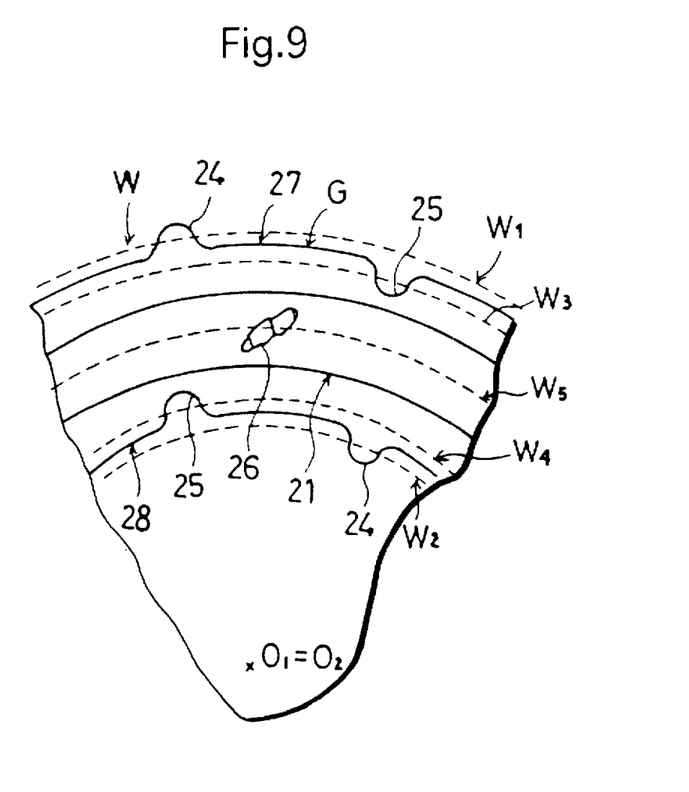
FIG. 9 is an explanatory view of a method for inspecting an O ring through picture processing.

As stated in the foregoing, upon incidence of reflected light into the end lens of the CCD camera 10 as shown in FIG. 5 and FIG. 7, expression in binary values are made so that the vicinity of the top 18 of the surface of the O ring 2 and the surface of the conveyor 31 or the conveyor 32 are expressed in white and an inner circumferential margin 19 and an outer circumferential margin 20 of the O ring 2 are expressed in black, and as shown in FIG. 8 and FIG. 9, an O ring picture G having a ring-shaped white portion 21 is obtained. If a surface flaw exists on the vicinity of the top 18, the surface flaw 26 is expressed in black in the ring-shaped white portion 21 as shown in FIG. 9.

In a flowchart shown in FIG. 6 and a view of a picture expressed in binary values shown in FIG. 8, a center of gravity $O_1$ of the O ring picture G expressed in binary values is subsequently calculated by the picture processing means 17 in FIG. 4, and a center $O_2$ of a window W, which is predetermined by inputting from the controlling portion 22, is moved to coincide with the center of gravity $O_1$.

The window W is concentric circles consisting of two windows for detecting a flash $W_1$, $W_2$, two windows for detecting a crack $W_3$, $W_4$, and a window for detecting a surface flaw $W_5$. The window W and the O ring picture G are displayed on the monitor 23 (see FIG. 4).

FIG. 9 shows a situation in which the center $O_2$ of the window W is coincided with the center of gravity $O_1$ of the O ring picture G, and in this case, a flash 24 and a crack 25 exist on each of outer circumference 27 and the inner circumference 28 of the O ring picture G and a surface flaw 26 exists in the ring-shaped white portion 21. The two windows $W_1$ and $W_3$ correspond to the outer circumference 27 of the O ring picture G and detect the flash 24 and the crack 25 on the outer circumference 27, and the two windows $W_2$ and $W_4$ correspond to the inner circumference 28 and detect the flash 24 and the crack 25 on the inner circumference 28, and the window $W_5$ corresponds to the ring-shaped white portion 21 along the center in the width direction thereof and detects the surface flaw 26.

Figure 6:
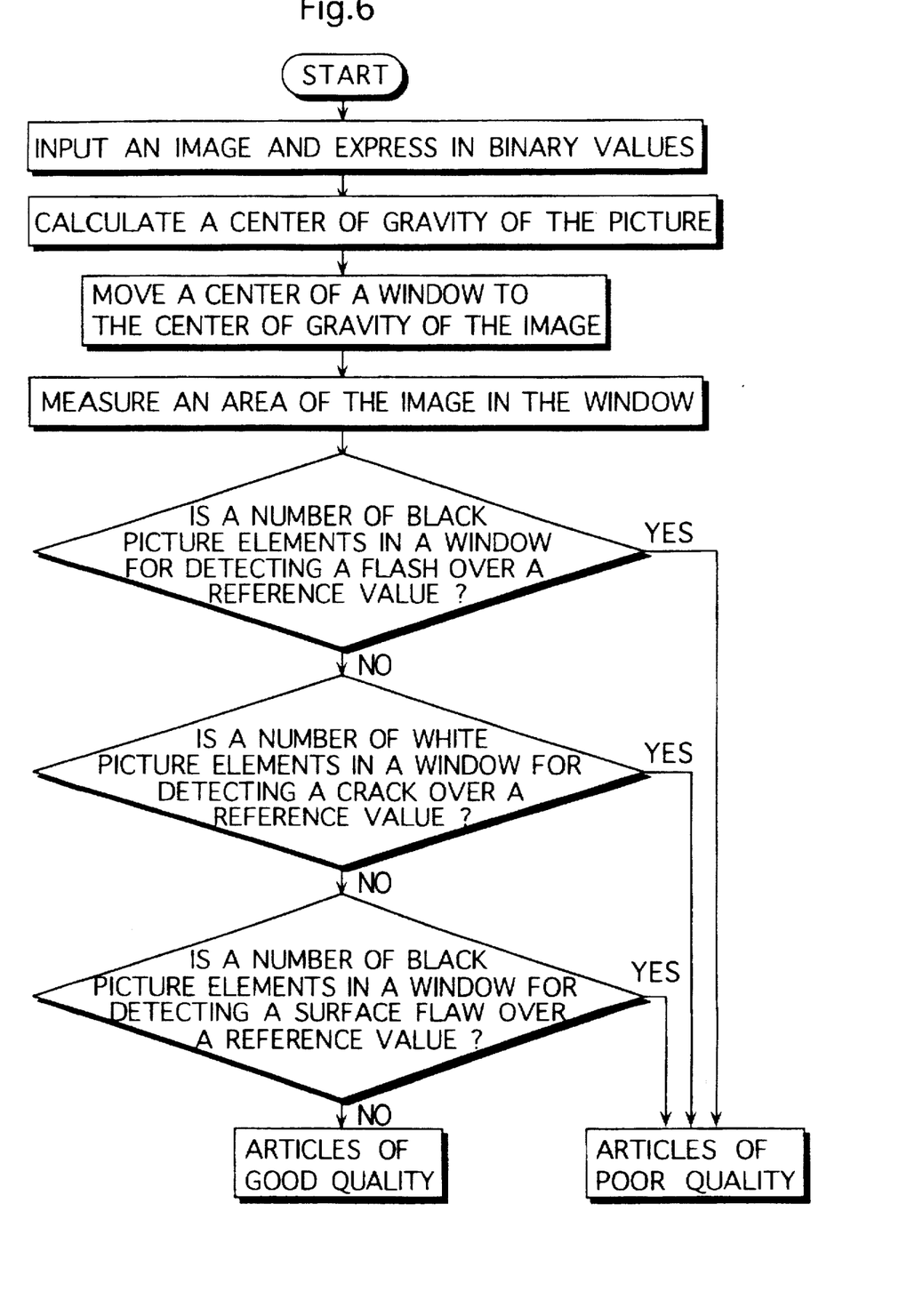
FIG. 6 is a flowchart of inspecting an O ring and judging acceptance or rejection.
Figure 10:
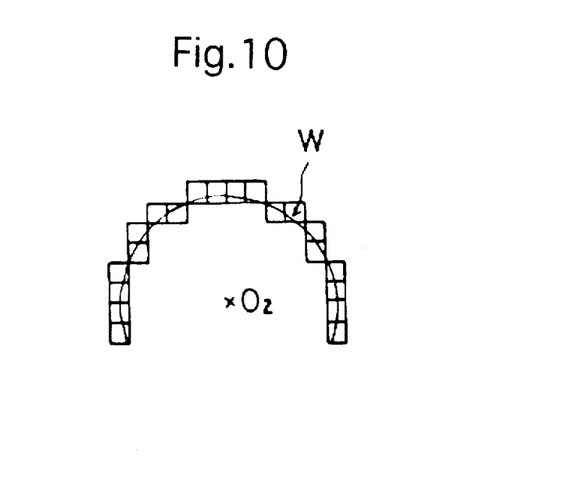
FIG. 10 is an explanatory view of a window.

In further detailed explanation, in FIG. 6, FIG. 9, and FIG. 10, the picture processing means 17 (see FIG. 4) measures an area in the window W, i.e. counts numbers of white picture elements and black picture elements in the window W as shown in FIG. 10, the numbers are compared with reference values for judging acceptance or rejection inputted beforehand, existence of a flash 24, a crack 25, or a surface flaw 26 beyond acceptable ranges is detected and judged, and whether quality of the O ring 2 is good or poor is decided. For example, if the O ring 2 does not have any flash 24, crack 25, nor surface flaw 26, numbers of black picture elements in the windows $W_1$, $W_2$, and $W_5$ are zero, and numbers of white picture elements in the windows $W_3$ and $W_4$ are zero.

If numbers of white picture elements and black picture elements are within acceptable ranges on all the windows $W_1$, $W_2$, $W_3$, $W_4$, and $W_5$, the O ring 2 is judged to be an article of good quality. On the contrary, if numbers of white picture elements and black picture elements are beyond the ranges, the O ring 2 is judged to be an article of poor quality. A signal of good or poor is sent to the controller 16 in FIG. 4, the controller 16 sends an instruction signal for operation toward the device for discharging articles of poor quality 7, and the device for discharging articles of poor quality 7 sends an O ring of poor quality into the box for articles of poor quality 46.

In the embodiment in FIG. 1, FIG. 2, and FIG. 4, the first inspecting means 41 comprises a CCD camera 10, a coaxial downward light projecting lamp 11, a sensor 6, a picture processing means 17, a controller 16, a controlling portion 22, and a monitor 23. The second inspecting means 42 is constructed in the same way.

It is possible to omit the screening machine 52.

In the apparatus explained in FIG. 4 and FIG. 6 to FIG. 10, dimensions of an inner diameter and an outer diameter of an O ring 2 are also inspected, therefore it is also possible to inspect mixing of O rings 2 of different sizes. Order of inspections in a flash, a crack, and a surface flaw in the flowchart shown in FIG. 6 can be freely changed, or they can be conducted synchronously.

Figure 11:
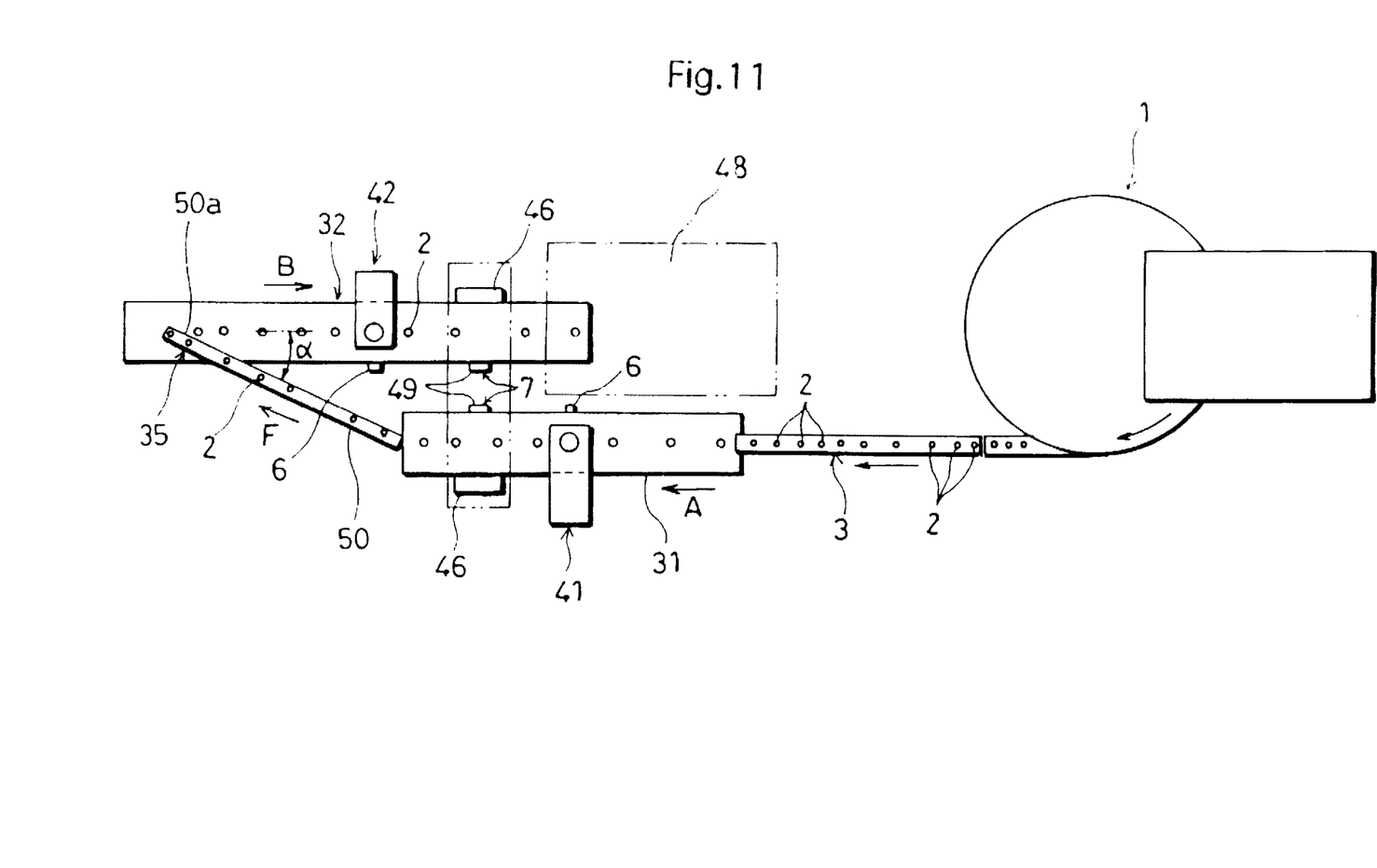
FIG. 11 is a top plan view of another embodiment of the apparatus for inspecting an O ring of the present invention.
Figure 12:
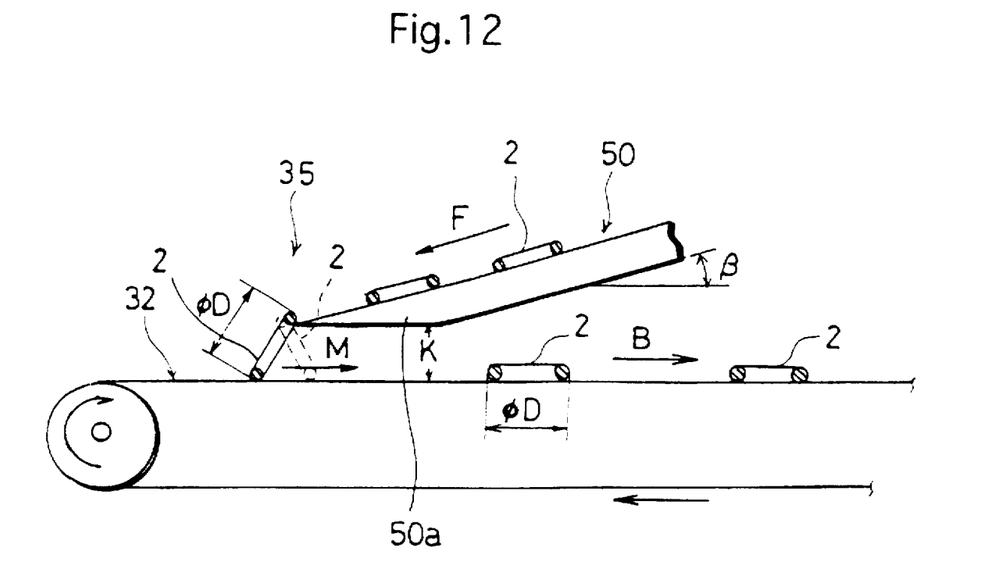
FIG. 12 is a front view in section of the apparatus for inspecting an O ring of FIG. 11.

Next, FIG. 11 and FIG. 12 show another embodiment of an apparatus for inspecting an O ring of the present invention, and FIG. 11 is a top plan view of the whole apparatus and FIG. 12 is an front view in section. In both of the drawings, O rings 2 are successively sent from a parts feeder 1 to a first conveyor 31 through a feeder for straight advance 3, and one side of each O ring is inspected at first by a first inspecting means 41, and a device for discharging articles of poor quality 7 discharges articles of poor quality into a box for articles of poor quality 46. In this case, an air blow nozzle 49 is used for the device for discharging articles of poor quality 7. That is to say, a high-speed air is emitted from a marginal side of the first conveyor 31 to the width direction of the conveyor 31 in order to discharge articles of poor quality into the box for articles of poor quality 46 placed on the other marginal side, and this shows that it is possible to use an air pressure like this besides a mechanical discharging mechanism as shown in FIG. 1 and FIG. 4. In this case, a screening machine 52 is omitted, however, it is also possible to arrange the screening machine 52 shown in FIG. 1 and FIG. 2 so that products (O rings 2) and flashes are screened and only the products are fed to the parts feeder 1.

Another feeder for straight advance 50 is placed at an rear end (downstream end) of the first conveyor 31. The feeder 50 successively receives O rings 2 fed from the first conveyor 31, gives the O rings 2 vibration and straight advance toward an arrow F, and drops the O rings 2 to an upstream end side of the second conveyor 32. In the illustration, the second conveyor 32 is arranged to be parallel with the first conveyor 31 in a plane view with their feeding directions opposite as shown with an arrow A and an arrow B, and the feeder for straight advance 50 is arranged to be oblique in a plane view and connects the rear end (downstream end) of the first conveyor 31 and the front end (upstream end) of the second conveyor 32.

Arrangement is made so that the feeding direction F of the feeder for straight advance 50 is opposite with the feeding direction B of the second conveyor 32 in a plane view. Moreover, a space K between a downstream end portion 50a of the feeder for straight advance 50 where O rings 2 drop and an upper face of the second conveyor 32 directly below the downstream end portion 50a is arranged to be slightly smaller than outer diameters D of O rings 2, and as shown with a solid line in FIG. 12, an O ring 2 is kept slant between a pointed end portion of the feeder for straight advance 50 and the upper face of the second conveyor 32 for a moment. However, because the feeding direction B of the second conveyor 32 is opposite with the feeding direction (the arrow F) of the feeder for straight advance 50, a bottom end of the O ring 2 is sent as shown with an arrow M owing to friction between the bottom end and the second conveyor 32, and the O ring 2 inverts and falls on the upper face of the second conveyor 32.

In other words, in FIG. 11 and FIG. 12, the inverting means 35 for inverting an O ring 2 comprises the feeder for straight advance 50 which is arranged so that the feeding direction F is opposite with the feeding direction B of the second conveyor 32 and that the downstream end portion 50a is placed above the upper face of the second conveyor 32 keeping a space K slightly smaller than outer diameters D of O rings 2.

The feeder for straight advance 50 is arranged to be inclined with a horizontal face at an angle β of approximately 15° to 30°. In a plane view, the feeder for straight advance 50 and the second conveyor 32 are arranged to have an angle α of approximately 30° at most, however, it is possible to arrange the second conveyor 32 directly below the first conveyor 31 so that the first conveyor 31, the feeder for straight advance 50, and the second conveyor 32 are placed on a line in a plane view.

In the present invention, in case the angle α is approximately 30° at most and the feeding direction of the feeder for straight advance 50 and the feeding direction of the second conveyor 32 are respectively toward F and B, the direction of the straight advance of the feeder for straight advance 50 is designated as "an opposite direction" with the feeding direction of the second conveyor 32 in a plane view.

As for the inverting means 35 as shown in FIG. 11 and FIG. 12, it is important to appropriately arrange the space K and an oscillation frequency and amplitude of the feeder for straight advance 50 in order to smoothly and securely invert O rings 2. In some cases, it is preferable to slightly slant the second conveyor 32 instead of arranging it horizontally.

O rings 2 inverted by the inverting means 35 are received and sent toward the arrow B by the second conveyor 32, and the second conveyor 32 is provided with a second inspecting means 42 having the same structure with the first inspecting means 41 of the first conveyor 31, a device for discharging articles of poor quality 7 arranged on downstream of the second inspecting means 42, and a box for articles of good quality 48 arranged at a downstream end of the second conveyor 32. Each first and second inspecting means 41 and 42 comprises a circuit, a CCD camera 10, a lamp 11, a picture processing means 17, a controller 16, and a monitor 23 similar to those in the foregoing embodiment shown in FIG. 4.

Needless to say, other changes are possible besides the illustrated embodiments described above. The vibration plate 61 can be a panting plate possessing small holes 59 and big holes 60 as stated above, or it can be wire netting. In case of wire netting, it is necessary to use wire netting having largeness of meshes corresponding to the small holes 59 and wire netting having largeness of meshes corresponding to the big holes 60. The feeding amount from the hopper 51 to the screening machine 52 needs to be adjusted to the screening ability of the screening machine 52. Moreover, it is also possible to change the method and order in which each of the first and second inspecting means 41 and 42 illuminates from a direction intersecting perpendicularly with the surface of the first or second conveyor 31, 32 and processes a picture G of a ring-shaped white portion 21 formed by a reflection of a surface of an O ring 2. Further more, the curved concave 36a of the inversion guide 36 is not limited to a fixed sliding face, and it is possible to arrange so that a lightly moving thin belt is shaped into a curved concave and is run along this curved concave.

According to the present invention, only products are automatically and accurately inspected on surface flaws preventing mixture of other kinds of product. In other words, removing flashes by hand is omitted and the present invention excels in operation efficiency. Moreover, the apparatus does not require a large space. As for the processing amount (screening amount) of the screening machine 52, an amount corresponding to the ability of detecting surface flaws is sufficient, therefore the screening machine 52 does not become large-sized.

In the present invention, both sides of an O ring 2 can be inspected automatically for detecting defects. Moreover, a time required for inspecting both sides of one O ring is approximately the same with a time required for inspecting one side of an O ring, and O rings are inspected with high efficiency. Inspecting surface flaws on both sides of each O ring increases reliability of the inspection, i.e. quality of O rings. Flashes 24, cracks 25, and differences in size are inspected twice, i.e. double check, and the inspection becomes more reliable.

If the vibration plate 61 is arranged to be detachable, it is possible to change vibration plates corresponding to sizes of products, and in case the vibration plate 61 is damaged, it can be easily changed to a new vibration plate 61.

O rings are inverted at a high speed corresponding to an extreme high speed of automatical inspection by the first and second inspecting means 41 and 42. This makes it possible to continuously inspect both sides of an O ring 2 without extending time for inspecting one side. For example, it is possible to realize high-speed inspection of 150/min for O rings 2 of a normal size.

The construction of the inverting means 35 can be simplified, and O rings are inverted smoothly and certainly.

While preferred embodiments of the present invention have been described in this specification, it is to be understood that the invention is illustrative and not restrictive, because various changes are possible within the spirit and indispensable features.

That is to say, as described in the foregoing, the vibration plate 61 can be a panting plate possessing small holes 59 and big holes 60, or it can be wire netting. In case of wire netting, it is necessary to use wire netting having largeness of meshes corresponding to the small holes 59 and wire netting having largeness of meshes corresponding to the big holes 60. The feeding amount from the hopper 51 to the screening machine 52 needs to be adjusted to the screening ability of the screening machine 52. Moreover, it is also possible to change the method and order in which each of the first and second inspecting means 41 and 42 illuminates from a direction intersecting perpendicularly with the surface of the first or second conveyor 31, 32 and processes a picture G of a ring-shaped white portion 21 formed by a reflection at a surface of an O ring 2. Further more, the curved concave 36a of the inversion guide 36 is not limited to a fixed sliding face, and it is possible to arrange so that a lightly moving thin belt is shaped into a curved concave and is run along this curved concave.

We claim:

1. An apparatus for inspecting an O ring, comprising:
   a first conveyor for successively carrying and sending O rings;
   a first inspecting means for detecting surface flaws of the O rings by illuminating from a direction intersecting perpendicularly with a surface of said first conveyor and processing pictures of ring-shaped white portions formed by reflections at surfaces of the O rings;

an inverting means placed at a rear end side of said first conveyor for inverting said O rings which are fed successively;

a second conveyor for receiving and sending the O rings inverted by said inverting means; and a second inspecting means for detecting surface flaws of the O rings by illuminating from a direction intersecting perpendicularly with a surface of said second conveyor and processing pictures of ring-shaped white portions formed by reflections at surfaces of the O rings.

wherein said first conveyor and said second conveyor cross at an acute angle of 15° to 60° as seen from a top plane view and the feeding direction of the second conveyor is substantially opposite, offset by said acute angle, to that of the first conveyor.

2. An apparatus for inspecting an O ring in which surface flaws of O rings are inspected by successively sending the O rings by a conveyor, inputting pictures of the O rings by illuminating the O rings, and processing the pictures, wherein the improvement comprises:

a vibrating screen for separating O rings and flashes removed from the O rings and feeding the O rings toward said conveyor, said vibration screen having:
  a first group of holes disposed at an upstream portion of said vibration screen, the flashes being separated by falling through said first group of holes; and
  a second group of holes larger than said first group of holes disposed at a midstream portion of said vibration screen, the O rings falling through said second group of holes and being lead to the conveyor; and a flash receiver disposed at a downstream side of said vibrating screen receiving the flashes not separated by said vibration screen.

3. An apparatus for inspecting an O ring, comprising:

a vibrating screen for separating O rings and flashes removed from the O rings;

a first conveyor for successively carrying and sending the O rings fed from said vibrating screen;

a first inspecting means for detecting surface flaws of the O rings by illuminating from a direction intersecting perpendicularly with a surface of said first conveyor and processing pictures of ring-shaped white portions formed by reflections at surfaces of the O rings;

an inverting means placed at a rear end side of said first conveyor for inverting said O rings which are fed successively;

a second conveyor for receiving and sending the O rings inverted by said inverting means; and a second inspecting means for detecting surface flaws of the O rings by illuminating from a direction intersecting perpendicularly with a surface of said second conveyor and processing pictures of ring-shaped white portions formed by reflections at surfaces of the O rings, wherein the first conveyor and the second conveyor cross at an acute angle of 15° to 60° as seen from a top plane view and the feeding direction of the second conveyor is substantially opposite, offset by said acute angle, to that of the first conveyor.

4. An apparatus for inspecting an O ring, comprising:

a first conveyor for successively carrying and sending O rings;

a first inspecting means for detecting surface flaws of the O rings by illuminating from a direction intersecting perpendicularly with a surface of said first conveyor and processing pictures of ring-shaped white portions formed by reflections at surfaces of the O rings;

an inverting means placed at a rear end side of said first conveyor for inverting said O rings which are fed successively;

a second conveyor for receiving and sending the O rings inverted by said inverting means; and a second inspecting means for detecting surface flaws of the O rings by illuminating from a direction intersecting perpendicularly with a surface of said second conveyor and processing pictures of ring-shaped white portions formed by reflections at surfaces of the O rings, wherein the inverting means is provided with an inversion guide possessing a curved concave surface which surrounds a U-turn portion at the rear end side of the first conveyor, the curved concave surface keeping a predetermined space from the U-turn portion.

5. An apparatus for inspecting an O ring, comprising:

a first conveyor for successively carying and sending O rings;

a first inspecting means for detecting surface flaws of the O rings by illuminating from a direction intersecting perpendicularly with a surface of said first conveyor and processing pictures of ring-shaped white portions formed by reflections at surfaces of the O rings;

an inverting means placed at a rear end side of said first conveyor for inverting said O rings which are fed successively;

a second conveyor for receiving and sending the O rings inverted by said inverting means; and a second inspecting means for detecting surface flaws of the O rings by illuminating from a direction intersecting perpendicularly with a surface of said second conveyor and processing pictures of ring-shaped white portions formed by reflections at surfaces of the O rings, wherein the inverting means is provided with a feeder for straight advance which is arranged so that the feeder for straight advance receives O rings sent from the first conveyor and gives the O rings vibration and straight advance in a direction opposite to the feeding direction of the second conveyor, and that a space between a downstream end portion of the straight advance where the O rings drop and an upper face of the second conveyor directly below the downstream end portion is slightly smaller than outer diameters of the O rings.

6. The apparatus for inspecting an O ring as set forth in any one of claim 1 or 3, wherein each first and second inspecting means comprises:

a CCD camera;

a lamp for projecting light possessing an optical axis which is coaxial with an optical axis of the CCD camera;

a sensor for detecting O rings sent to a place for inspection;

a controller where a detection signal from said sensor is inputted; and a picture processing means where an instruction signal from the controller is inputted for comparing with a reference value for judging acceptance or rejection and detecting and judging existence of a big surface flaw beyond an acceptable range.

7. The apparatus for inspecting an O ring as set forth in any one of claim 1 or 3, wherein the apparatus is provided with a device for discharging articles of poor quality comprising:

a member for horizontally moving on a conveyor and throwing rings toward a horizontal direction; and an actuator for operating said member on receipt of a signal from a controller.

8. The apparatus for inspecting an O ring as set forth in any one of claim 2 or 3, wherein the screening machine is provided with a vibration plate having small holes which diameters are smaller than inner diameters of O rings and big holes which diameters are larger than outer diameters of the O rings and said vibration plate is detachable.

9. The apparatus for inspecting an O ring as set forth in any one of claim 2 or 3, wherein the screening machine is provided with a vibration plate consisting of wire netting.

10. The apparatus for inspecting an O ring as set forth in claim 8, wherein the apparatus possesses a feeder for straight advance which feeds O rings from a parts feeder to a conveyor and a vibration plate is placed above said parts feeder.

11. The apparatus for inspecting O ring as set forth in claim 9, wherein the apparatus possesses a feeder for straight advance which feeds O rings from a parts feeder to a conveyor and a vibration plate is placed above said parts feeder.

12. An apparatus for inspecting an O ring, comprising:

a vibrating screen for separating O rings and flashes removed from the O rings;

a first conveyor for successively carrying and sending the O rings fed from said vibrating screen;

a first inspecting means for detecting surface flaws of the O rings by illuminating from a direction intersecting perpendicularly with a surface of said first conveyor and processing pictures of ring-shaped white portions formed by reflections at surfaces of the O rings;

an inverting means placed at a rear end side of said first conveyor for inverting said O rings which are fed successively;

a second conveyor for receiving and sending the O rings inverted by said inverting means; and a second inspecting means for detecting surface flaws of the O rings by illuminating from a direction intersecting perpendicularly with a surface of said second conveyor and processing pictures of ring-shaped white portions formed by reflections at surfaces of the O rings, wherein the inverting means is provided with an inversion guide possessing a curved concave surface which surrounds a U-turn portion at the rear end side of the first conveyor, the curved concave surface keeping a predetermined space from the U-turn portion.

13. An apparatus for inspecting an O ring, comprising:

a vibrating screen for separating O rings and flashes removed from the O rings;

a first conveyor for successively carrying and sending the O rings fed from said vibrating screen;

a first inspecting means for detecting surface flaws of the O rings by illuminating from a direction intersecting perpendicularly with a surface of said first conveyor and processing pictures of ring-shaped white portions formed by reflections at surfaces of the O rings;

an inverting means placed at a rear end side of said first conveyor for inverting said O rings which are fed successively;

a second conveyor for receiving and sending the O rings inverted by said inverting means; and a second inspecting means for detecting surface flaws of the O rings by illuminating from a direction intersecting perpendicularly with a surface of said second conveyor and processing pictures of ring-shaped white portions formed by reflections at surfaces of the O rings, wherein the inverting means is provided with a feeder for straight advance which is arranged so that the feeder for straight advance receives O rings sent from the first conveyor and gives the O rings vibration and straight advance in a direction opposite to the feeding direction of the second conveyor, and that a space between a downstream end portion of the straight advance where the O rings drop and an upper face of the second conveyor directly below the downstream end portion is slightly smaller than outer diameters of the O rings.

* * * * *